US010524921B2

(12) United States Patent
Goodman

(10) Patent No.: US 10,524,921 B2
(45) Date of Patent: Jan. 7, 2020

(54) UNIVERSAL JOINT IMPLANT FOR SHOULDER

(71) Applicant: Floyd G. Goodman, Williamston, MI (US)

(72) Inventor: Floyd G. Goodman, Williamston, MI (US)

( * ) Notice: Subject to any disclaimer, the term of this patent is extended or adjusted under 35 U.S.C. 154(b) by 72 days.

(21) Appl. No.: 15/932,543

(22) Filed: Mar. 13, 2018

(65) Prior Publication Data

US 2018/0271669 A1 Sep. 27, 2018

Related U.S. Application Data

(60) Provisional application No. 62/601,205, filed on Mar. 14, 2017.

(51) Int. Cl.
*A61F 2/40* (2006.01)
*A61F 2/30* (2006.01)

(52) U.S. Cl.
CPC ........ *A61F 2/4014* (2013.01); *A61F 2/30749* (2013.01); *A61F 2/40* (2013.01); *A61F 2/4059* (2013.01); *A61F 2002/3065* (2013.01); *A61F 2002/30331* (2013.01); *A61F 2002/30364* (2013.01); *A61F 2002/30495* (2013.01); *A61F 2002/30578* (2013.01); *A61F 2002/30624* (2013.01); *A61F 2002/30649* (2013.01); *A61F 2002/30658* (2013.01);

(Continued)

(58) Field of Classification Search
CPC ........ A61F 2/40; A61F 2/4014; A61F 2/4081; A61F 2/38; A61F 2002/30624; A61F 2002/30649; A61F 2002/3065; A61F 2002/30652

See application file for complete search history.

(56) References Cited

U.S. PATENT DOCUMENTS 3,869,730 A * 3/1975 Skobel ............... A61F 2/30742
623/19.12
4,550,450 A 11/1985 Kinnett
(Continued)

OTHER PUBLICATIONS

ASTM F 75-07, 2007.
(Continued)

*Primary Examiner* — Brian A Dukert
(74) *Attorney, Agent, or Firm* — Christopher John Rudy

(57) ABSTRACT

Universal joint implant includes an artificial glenohumeral component having articulating surfaces. The artificial glenohumeral component can include a first portion for articulation against an artificial glenoid surface or natural glenoid of the patient, and second portion(s) for articulation against an artificial humeral surface or resected, natural humerus; and a universal joint connection. The connection includes a yoke to provide for a center of movement generally within or adjacent a volume defined by an upper head of a normal humerus, which otherwise would be resected; and a substantially spheroidal body, at least in part, dissected, yet connected to provide the yoke; a body pivotable with respect to the yoke for providing motion in a first direction; a rotatable glenoid fixing member, rotatably fixable about the artificial glenoid surface or natural or resected glenoid; and a rotatable humeral fixing member, rotatably fixable about the artificial humeral surface or resected humerus.

20 Claims, 18 Drawing Sheets

(52) U.S. Cl.
CPC ............. *A61F 2002/30736* (2013.01); *A61F 2002/4007* (2013.01); *A61F 2002/4018* (2013.01); *A61F 2002/4051* (2013.01); *A61F 2002/4085* (2013.01)

(56) References Cited

U.S. PATENT DOCUMENTS

| | | |
|---|---|---|
| 5,462,575 A | 10/1995 | Del Corso |
| 6,248,132 B1 | 6/2001 | Harris |
| 6,953,478 B2 | 10/2005 | Bouttens et al. |
| 7,959,680 B2 | 6/2011 | Stone et al. |
| 9,259,508 B2 | 2/2016 | Serafin, Jr. et al. |
| 9,561,111 B1 | 2/2017 | Goodman |
| 2004/0039449 A1 | 2/2004 | Tornier |
| 2006/0079963 A1 | 4/2006 | Hansen |

OTHER PUBLICATIONS

ASTM F 136-08, 2008.
ASTM F 138-08, 2008.
ASTM F 621-08, 2008.
ASTM F 799-99, 1999.
ASTM F 2393-04, 2004.
Carpenter Technology Corporation, BioDur CCM Plus Alloy.
Goodman, Floyd G., "Universal Joint Implant for Shoulder," U.S. Appl. No. 62/601,205, filed Mar. 14, 2017.
Murphy, L. et al., "Acromion-fixation of glenoid components in total shoulder arthroplasty," J. Biomechanics, vol. 38, pp. 1702-1711, 2005.

\* cited by examiner

SCAPULA
HUMERUS

VIEW TRUE TO
MEDIAN PLANE
(LEFT LATERAL)

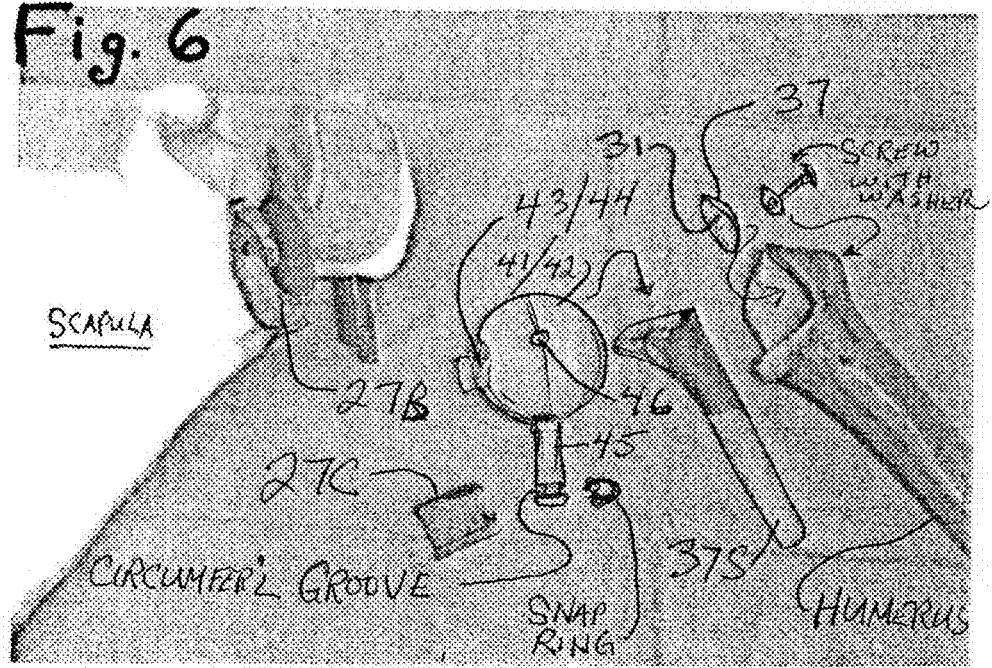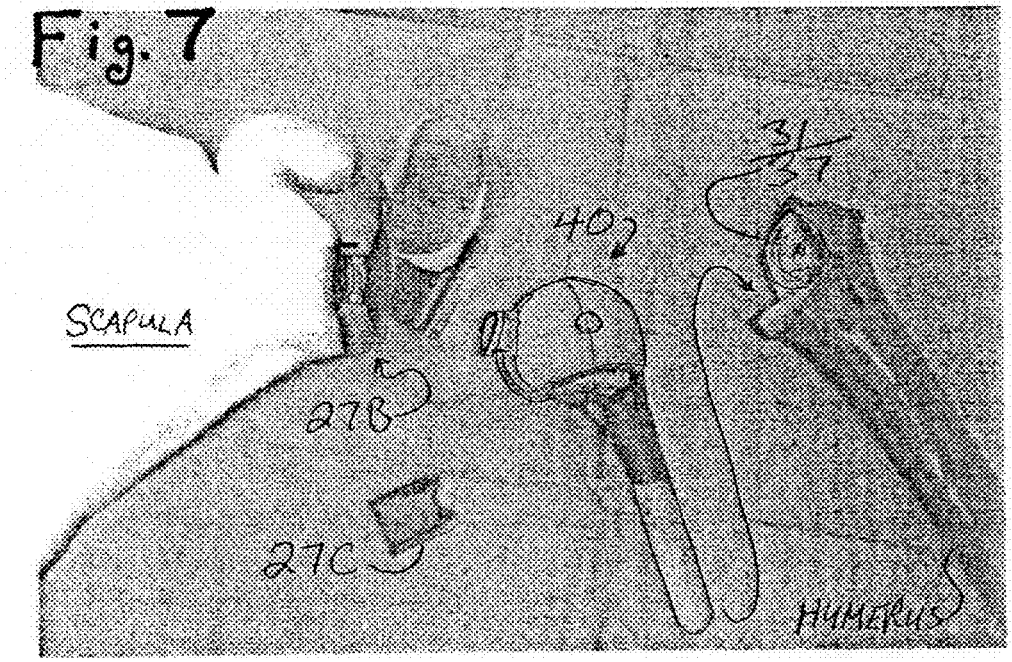

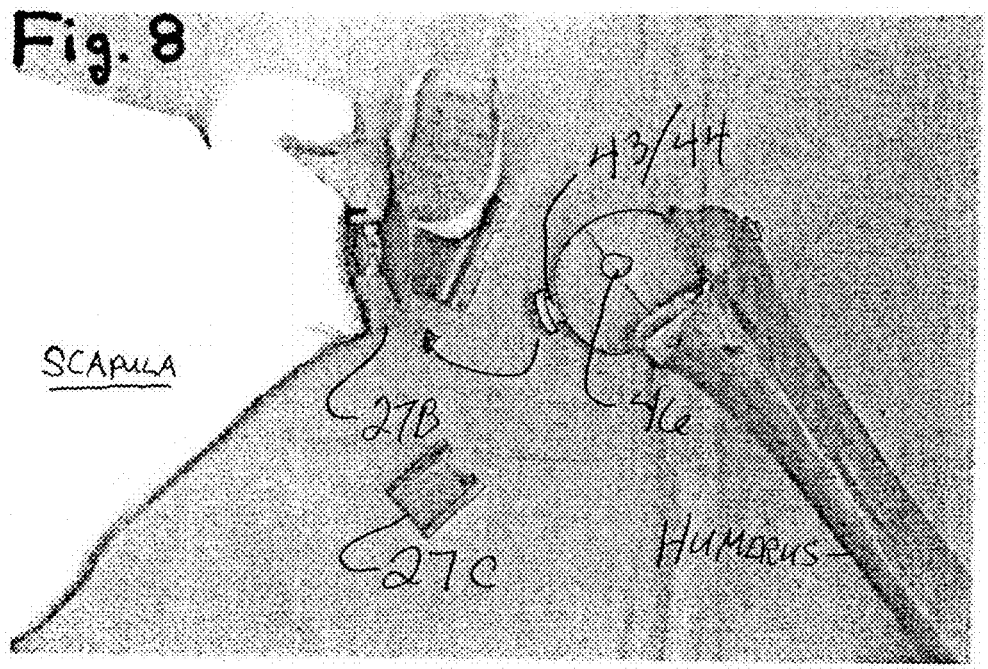
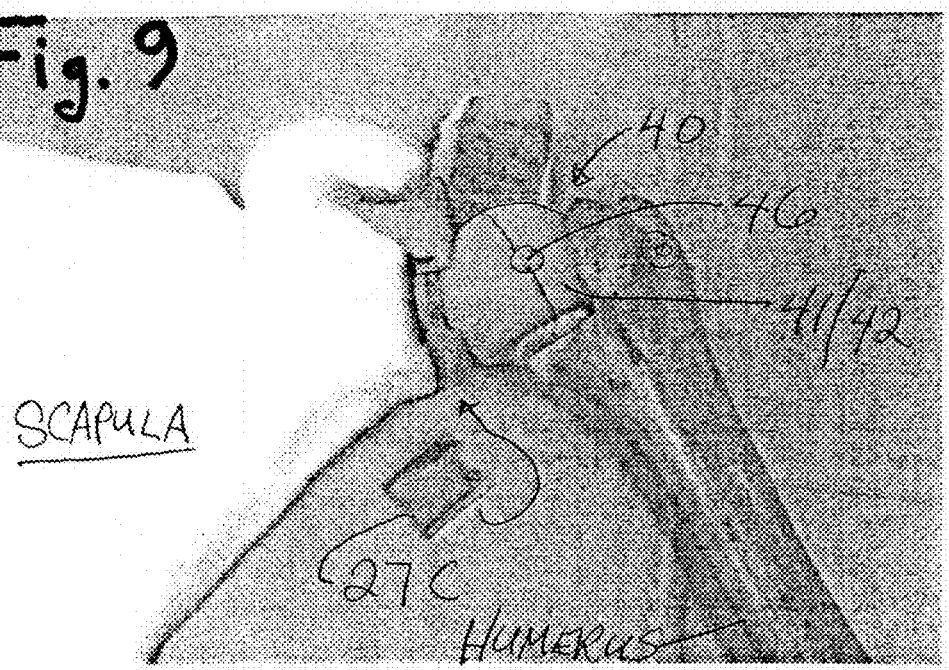

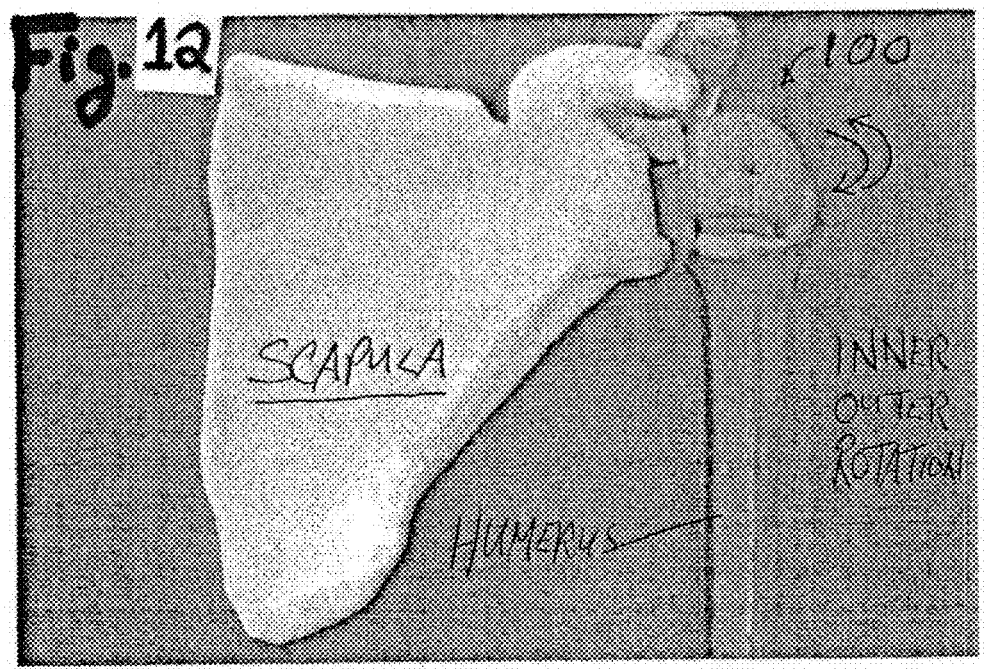
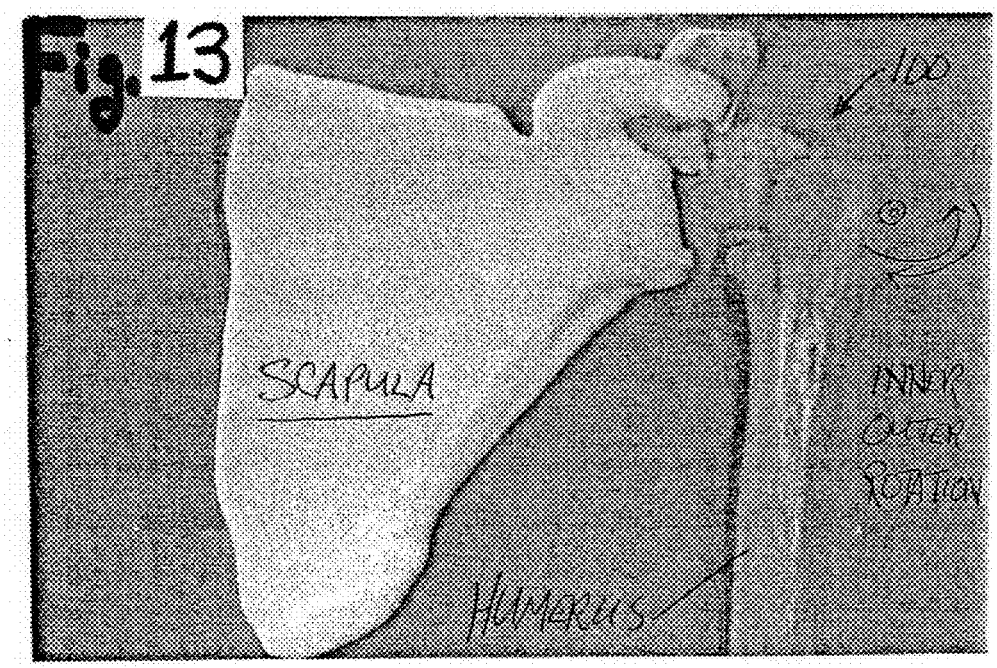

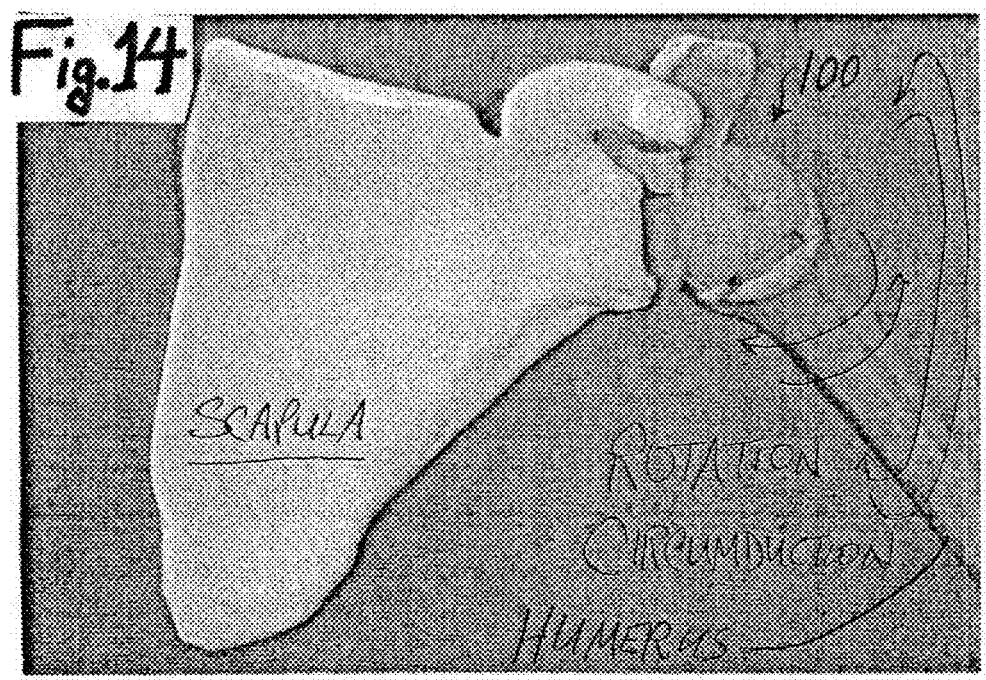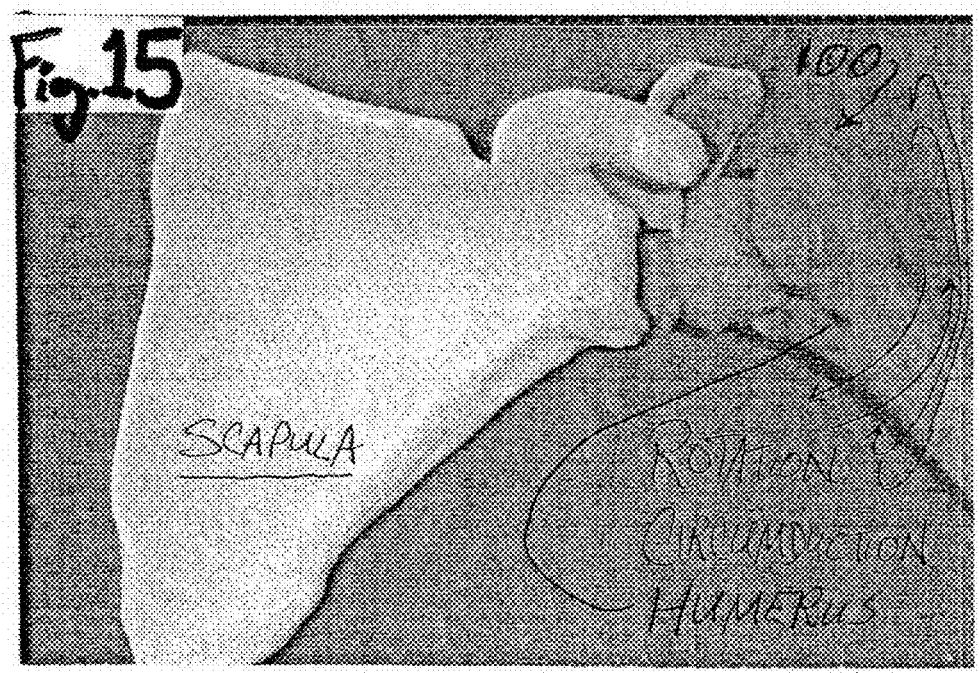

UNIVERSAL JOINT IMPLANT FOR SHOULDER

This claims benefits under 35 USC 119(e) of U.S. provisional patent application No. 62/601,205 filed on Mar. 14, 2017 A. D. The specification of that application, to include its drawings, is incorporated herein by reference in its entirety.

FIELD OF THE INVENTION

This concerns a universal joint-containing glenohumeral joint implant/component.

BACKGROUND TO THE INVENTION

Various shoulder joint implant art is known, to include ensembles for total or perhaps partial joint replacement of the main shoulder joint, i.e., the glenohumeral joint. Conventional configurations of those attempt to mimic the natural glenohumeral joint, generally having an implanted artificial humeral component with a ball-like head, say, of metal or ceramic, which articulates in and against a generally shallow open cup, say, of polyethylene or metal, of an implanted artificial glenoid component in a total arthroplasty or perhaps against the natural glenoid cup in a hemiarthroplasty. As good as such art can be, it is not without its drawbacks. Among these are difficulties in achieving natural range of motion; and the shoulder—being an enarthrodial joint, and the joint of the body with the greatest range of motion as in nature its head is held in place to a great extent by means of muscle, fibrous capsule and ligamentous tendon structures in a shallow cup, i.e., the glenoid cup—can be prone to dislocation, even after joint replacement surgery with a device of such art. The most frequent cause of unsuccessful shoulder joint replacement is failure of fixation through loosening of glenoid components, not infrequently caused by compromise of mounting of a metal shell holding the cup, or compromise of a cemented plastic cup, to a surgically prepared portion on the quite thin and fragile scapular bone, i.e., glenoid area. This deficit of glenoid area supporting bone may need to be addressed. Reverse shoulder implants are also known, in which a ball head is provided as part of the glenoid component, with a corresponding cup as part of the humeral component. Such art, too, is not without drawbacks, among which may include dislocation and/or glenoid component loosening as with the more anatomically conventional shoulder joint implants discussed in general above. Compare, the following art:

U.S. Pat. No. 4,550,450 to Kinnett, for a total shoulder prosthesis system.

U.S. Pat. No. 6,248,132 B1 to Harris, for a hip replacement prosthesis.

U.S. Pat. No. 6,953,478 B2 to Bouttens et al. for a shoulder prosthesis assembly.

U.S. Pat. No. 7,959,680 B2 to Stone et al., for a method and apparatus for performing a shoulder implant procedure.

Publication No. US 2004/0039449 A1 of Tornier, for a shoulder or hip prosthesis facilitating abduction.

Publication No. US 2006/0079963 A1 of Hansen, for a semi-constrained shoulder prosthetic for treatment of rotator cuff arthroplasty.

Murphy, L., and Prendergast, P., *J. Biomechanics,* 38 (2005), pages 1702-1711, "Acromion-fixation of glenoid components in total shoulder arthroplasty."

In address of the foregoing, U.S. Pat. No. 9,561,111 B1 to Goodman—which is incorporated herein by reference in its entirety, to include its drawings—discloses a shoulder joint implant. It captures or fixes humeral and glenoid components and employs a yoke-containing universal joint connection. As excellent as the art of that Goodman patent is, it, too, is not without drawbacks. Among these are, in certain embodiments, a potential for substantial scar-tissue ingrowth, and possible pathogenic growth; a tendency to require resection of a substantial amount of bone; and a certain bulkiness, especially in encapsulated embodiments.

It would be desirable to improve upon the art. It would be desirable, in particular, to provide a shoulder joint implant that ameliorates if not solves in general one or more of the problems in the art, notably dislocation, loosening and/or supporting bone deficit of the glenoid area, and range of motion. Furthermore, it would be desirable to reduce any potential for possibly detrimental scar-tissue ingrowth, and possible pathogenic growth; to conserve bone; and to streamline the configuration and maintain a more limited size of the implant. Additionally, it would be desirable to provide alternative(s) to the art.

A FULL DISCLOSURE OF THE INVENTION

Provided, in general, is a universal joint implant for a shoulder of a patient. It comprises an artificial glenohumeral component, which is useful in or as an ensemble for total joint replacement arthroplasty of the glenohumeral joint or in hemiarthroplasty in the glenohumeral joint, wherein:

the artificial glenohumeral component has articulating surfaces, which can include a first portion for articulation against an artificial glenoid surface or natural glenoid of the patient, and second portion(s) for articulation against an artificial humeral surface or resected, natural humerus; and the artificial glenohumeral component has a universal joint connection, which allows limited freedom of movement in any direction while transmitting rotary motion, and which includes:

a yoke, which can provide for a center of movement generally within or adjacent a volume defined by an upper head of a normal humerus, which otherwise would be resected and absent when the artificial glenohumeral component is implanted;

a substantially spheroidal body, at least in part, dissected and yet connected to provide the yoke;

a body pivotable with respect to the yoke for providing motion in a first direction;

a rotatable glenoid fixing member, rotatably fixable about the artificial glenoid surface or natural or resected glenoid; and a rotatable humeral fixing member, rotatably fixable about the artificial humeral surface or resected humerus.

Additional component(s) may be provided. Thus provided, for instance, may be a glenoid augment that provides the artificial glenoid surface, which may be provided to have an articulating surface in a form of a glenoid cup and/or a humeral augment that provides the artificial humeral surface, which may have an articulating surface in a form of a cup for resected humerus. As well, provided can be a glenoid receptacle can be provided to receive the rotatable glenoid fixing member rotatably and/or a humeral receptacle to receive the rotatable humeral fixing member rotatably, for example, in a form of an intramedullary humeral stem, which may include the humeral receptacle.

The invention is useful in connection with orthopedic repair of the shoulder.

Significantly, by the invention, not only is an alternative provided the art, but the art is advanced in kind, and one or more of its problems is ameliorated if not solved in general. Potential for substantial scar-tissue ingrowth, and possible pathogenic growth can be reduced; bone can be conserved, especially now in the humerus, to include, as a patient's condition may present, in the humeral head; and the configuration is streamlined to maintain a more limited implant size, which can assist in maintaining more natural motion and more full range of motion, to include by provision or restoration of a center of rotation more likened to that of a normal shoulder, which contributes to a reduction of the propensity for, if not occurrence of, dislocation. Furthermore, improved stability in a rotator cuff deficient shoulder can be provided, even in cases where viable rotator cuff structures are compromised or absent, and loosening of a glenoid prosthetic component may be lessened or prevented. Glenoid component stability may be enhanced through multi-point fixation, and glenoid area supporting bone deficit area can be addressed more fully. Implantation can be carried out by a wide range of nearly all orthopedic surgeons, not just the most skilled. Numerous further advantages attend the invention.

The instant invention is useful in arthroplasty.

The drawings form part of the specification hereof. With respect to the drawings, which are not necessarily drawn to scale, the following is briefly noted:

FIG. 6 is another exploded view of the implanted ensemble of FIG. 1.

FIG. 7 is another exploded view of the implanted ensemble of FIG. 1, in a more full state of assembly than that which is depicted in FIG. 6.

FIG. 8 is another exploded view of the implanted ensemble of FIG. 1, in a more full state of assembly that that which is depicted in FIG. 7.

FIG. 9 is another exploded view of the implanted ensemble of FIG. 1, in a more full state of assembly that that which is depicted in FIG. 8.

Figure 1:
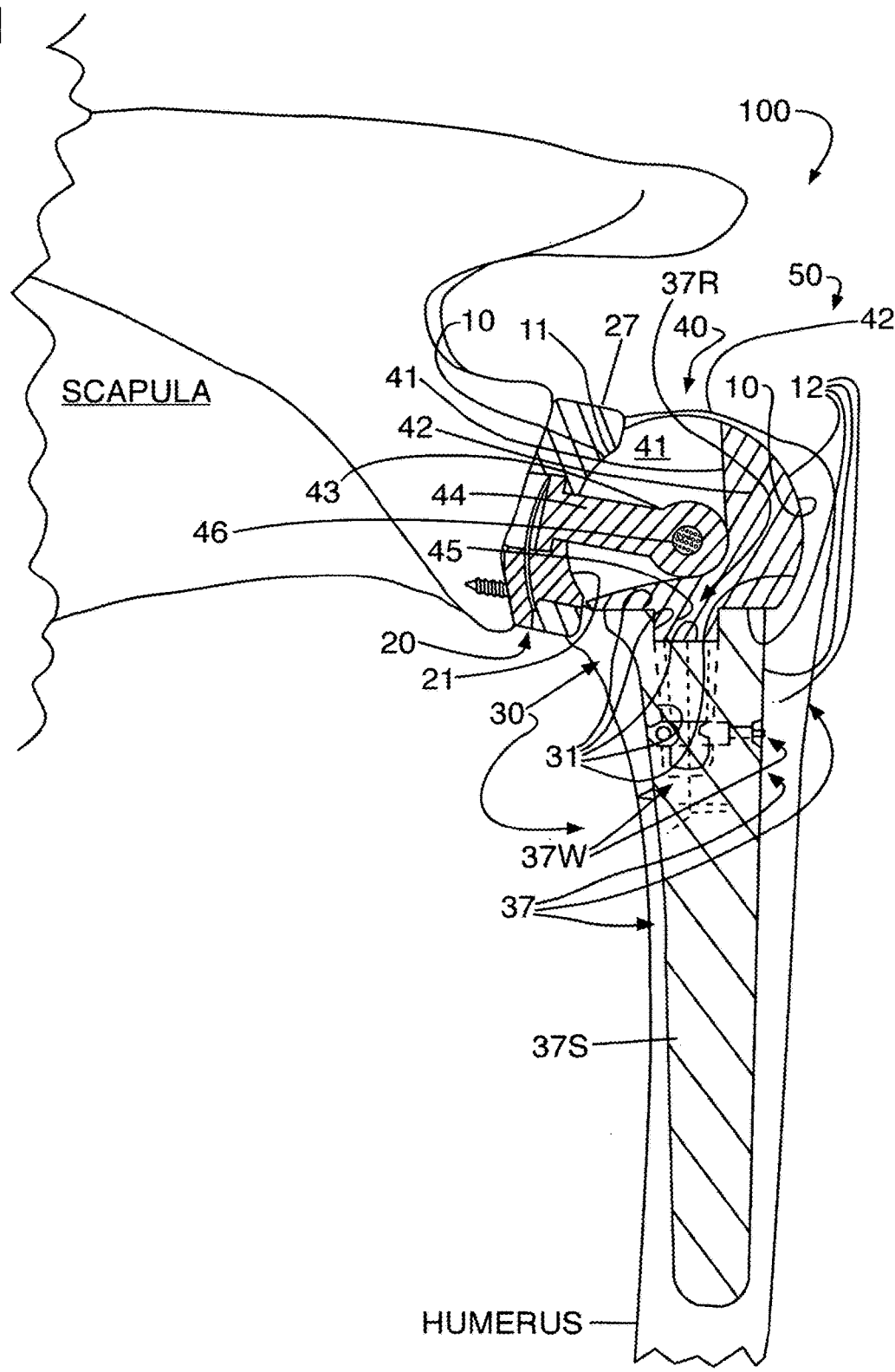
FIG. 1 is an elevational plan view of a universal joint implant ensemble implanted in a shoulder, here, the left shoulder of a human patient.
Figure 2:
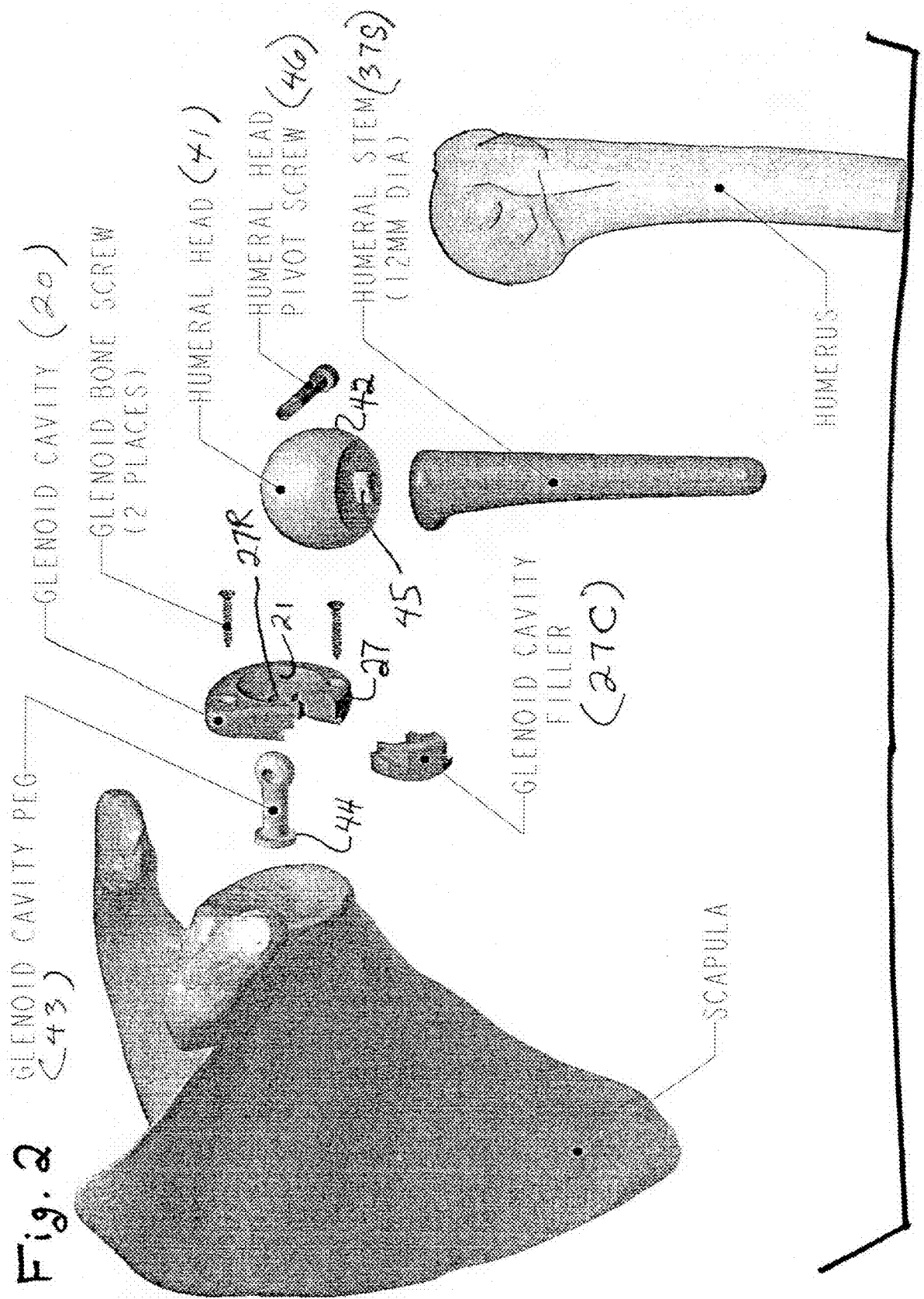
FIG. 2 is an exploded view of the ensemble with shoulder of FIG. 1.
Figure 3:
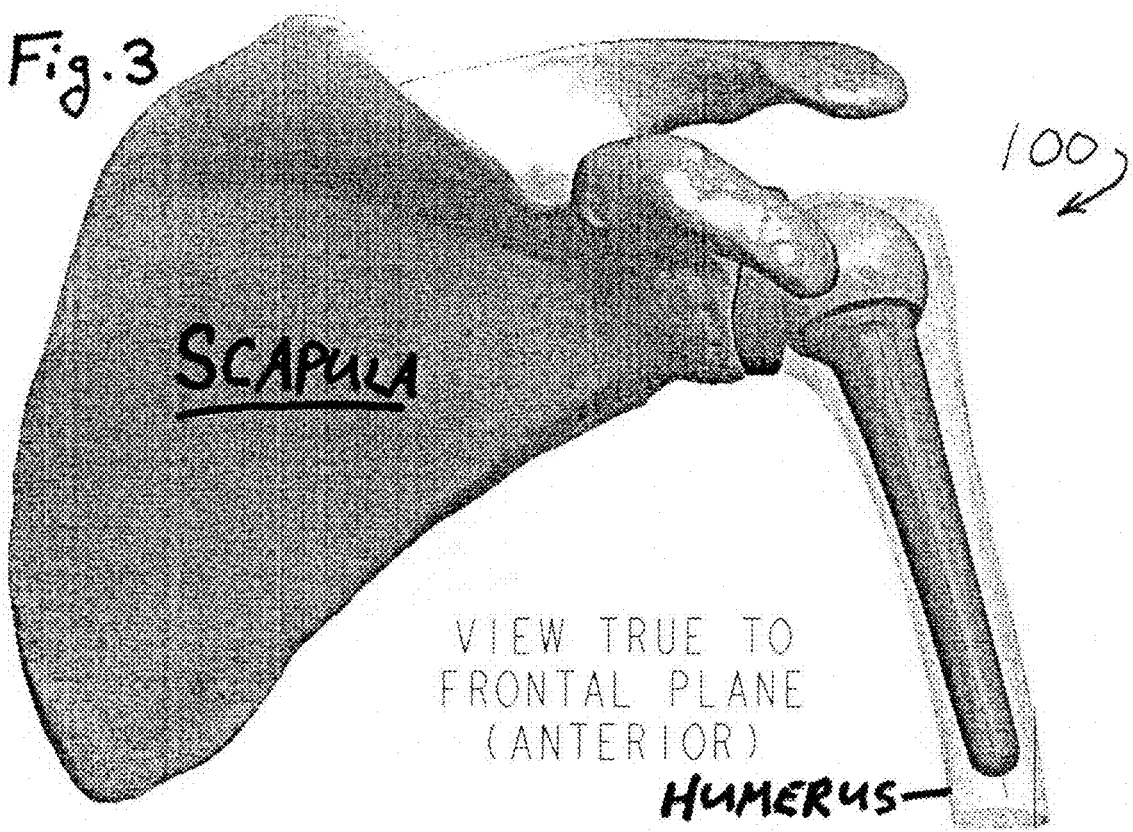
FIG. 3 is an anterior view of the implanted ensemble of FIG. 1.
Figure 4:
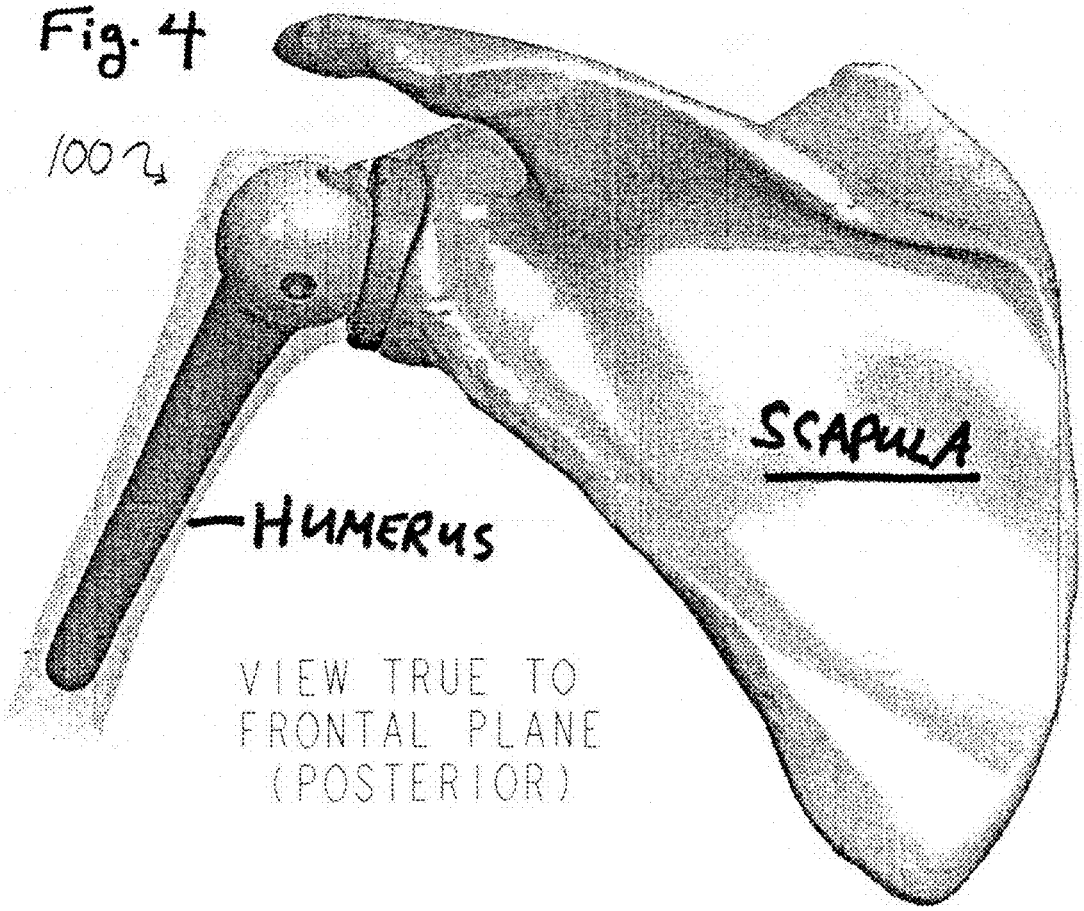
FIG. 4 is a posterior view of the implanted ensemble of FIG. 1.
Figure 5:
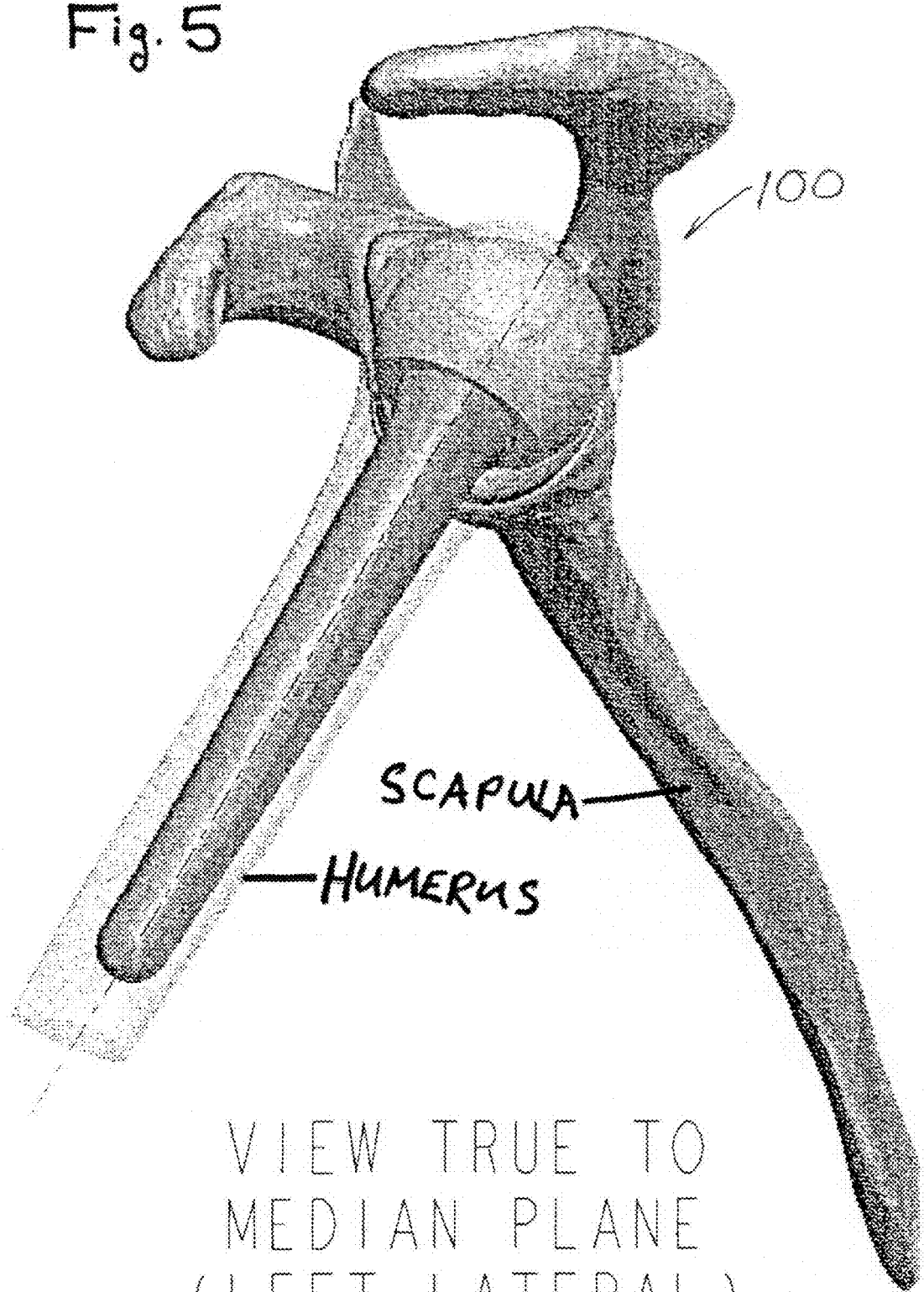
FIG. 5 is a left lateral view of the implanted ensemble of FIG. 1.
Figure 10:
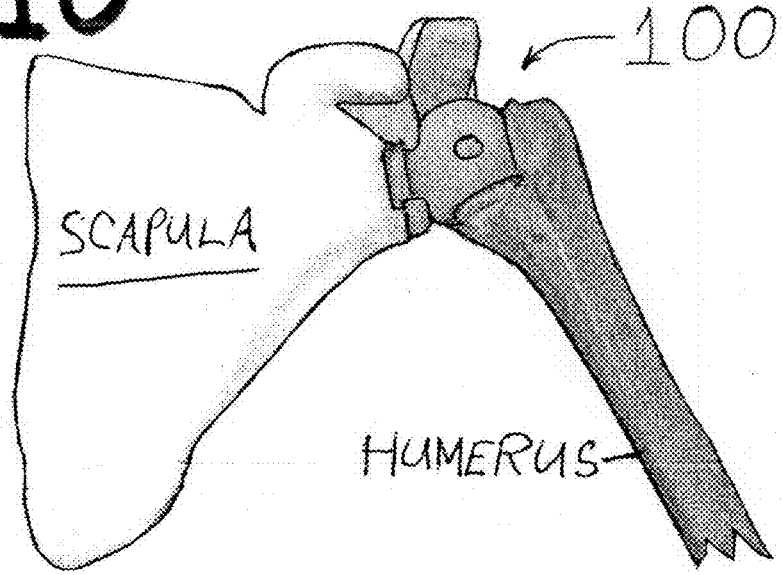
FIG. 10 is an elevational view of the implanted ensemble of FIG. 1, fully assembled from that which is depicted in FIG. 9.
Figure 11:
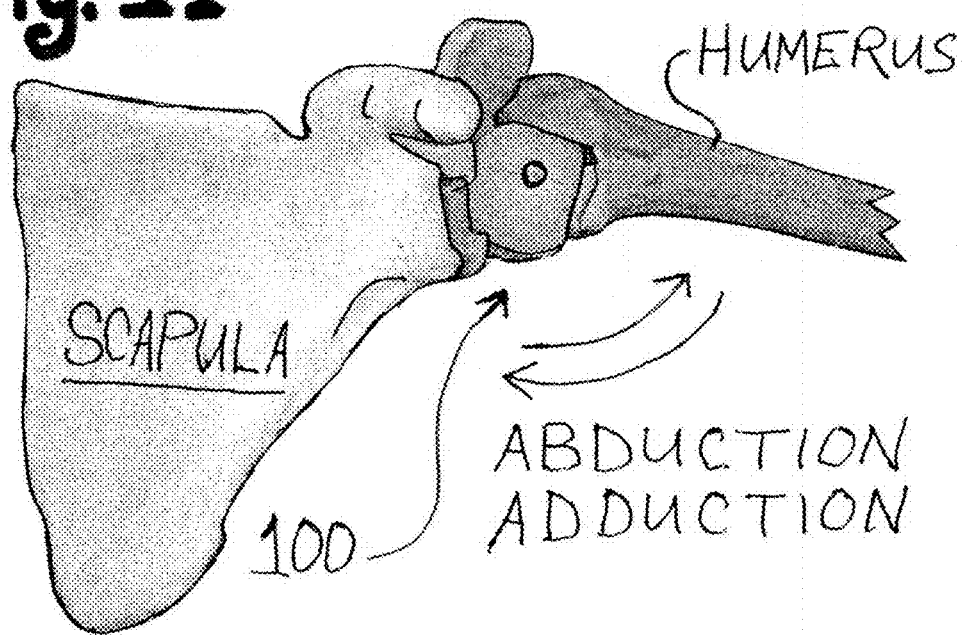

FIGS. 11-15 are elevational views of the implanted ensemble of FIGS. 1 and 9, showing some motions of the implant: abduction and adduction (FIG. 11); inner rotation and outer rotation (FIGS. 12 and 13); rotation and circumduction (FIGS. 14 and 15).

Figure 16:
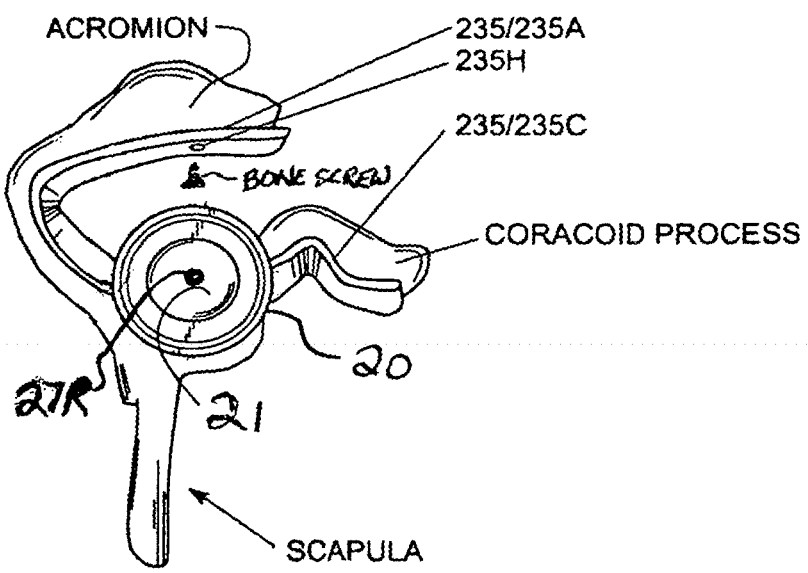

FIG. 16 is an elevational view of a glenoid component that can be used as part of a universal joint implant ensemble hereof, showing multi-point fixation.

Figure 17:
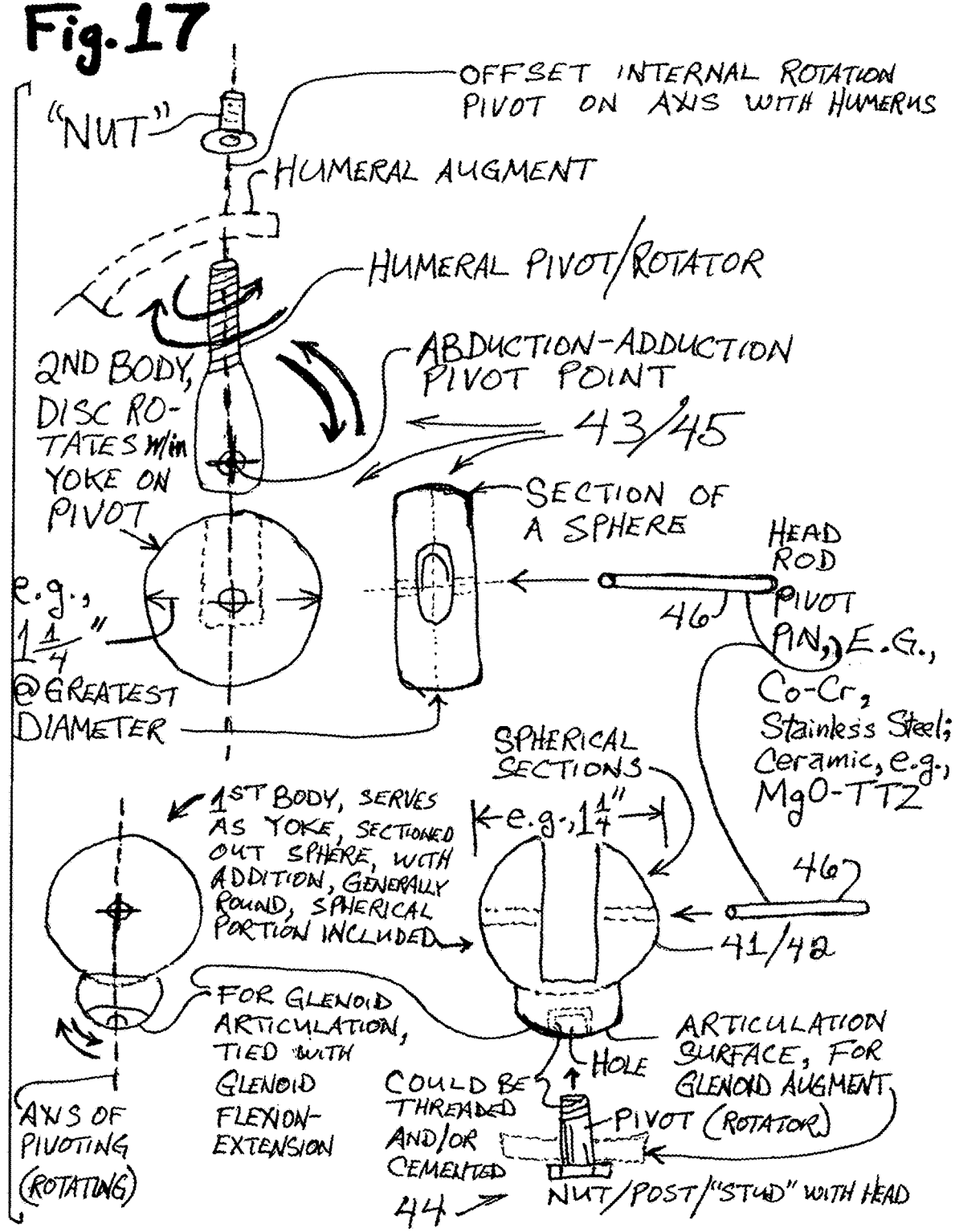

FIG. 17 is an exploded plan view of another embodiment of a universal joint implant ensemble hereof.

Figure 18:
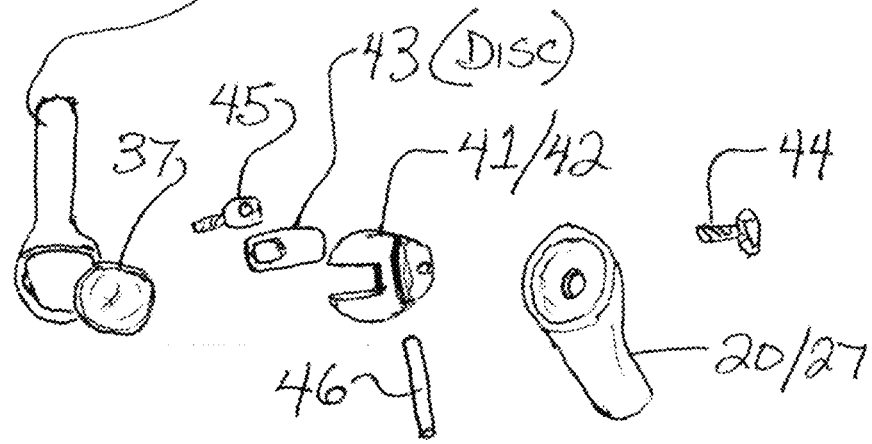

FIG. 18 is an exploded view of a universal joint implant ensemble hereof such as otherwise depicted in FIG. 17.

Figure 19:
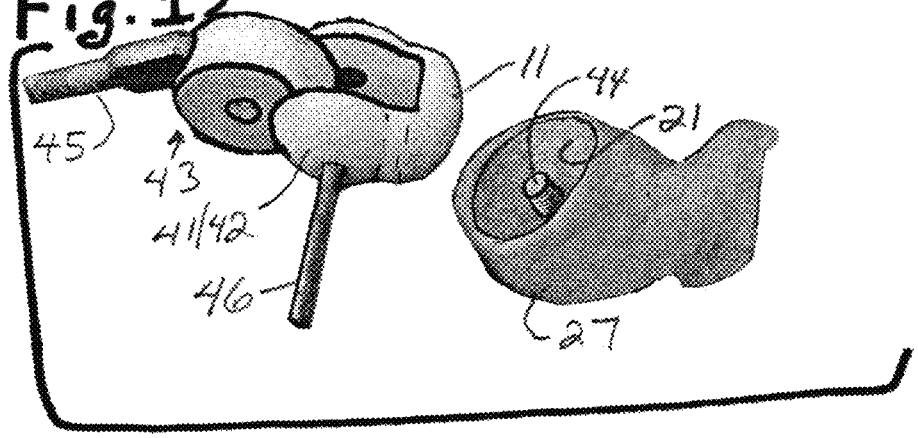

FIG. 19 is an exploded view of the ensemble of FIG. 18, in a more ordered state of assembly than that of FIG. 18.

Figure 20:
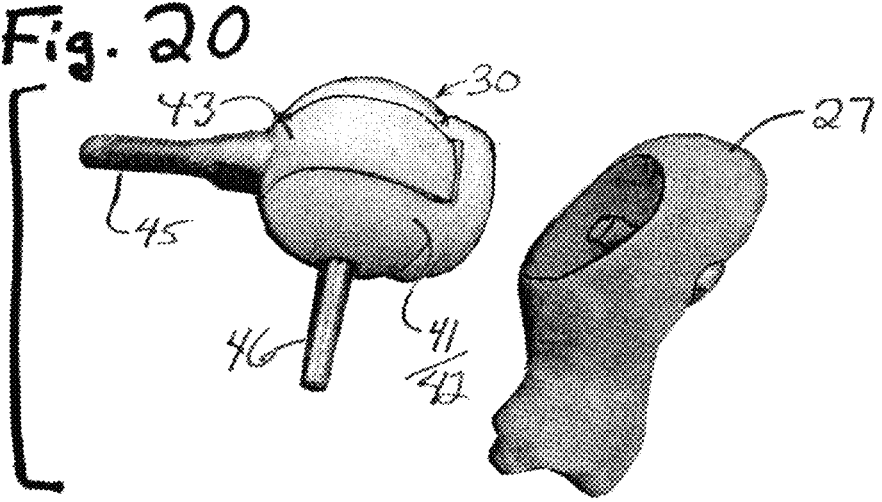

FIG. 20 is an exploded view of the ensemble of FIG. 18, in a more ordered state of assembly than that which is depicted in FIG. 19.

Figure 21:
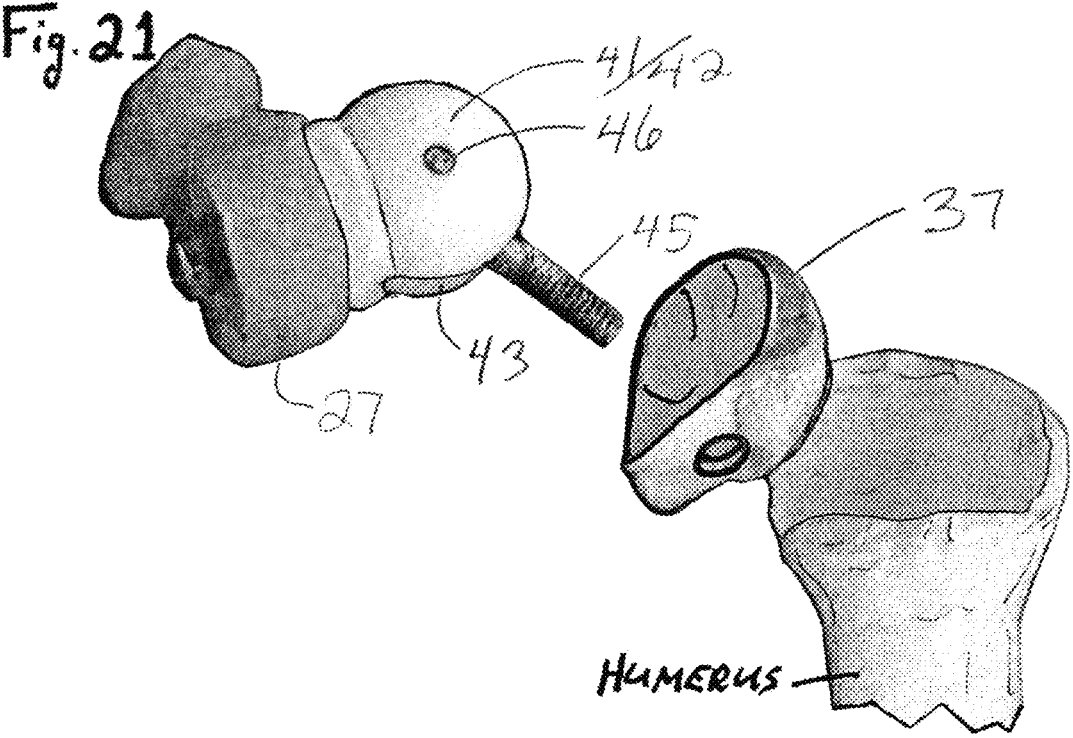

FIG. 21 is an exploded view of the ensemble of FIG. 18, in a more ordered state of assembly than that which is depicted in FIG. 20.

Figure 22:
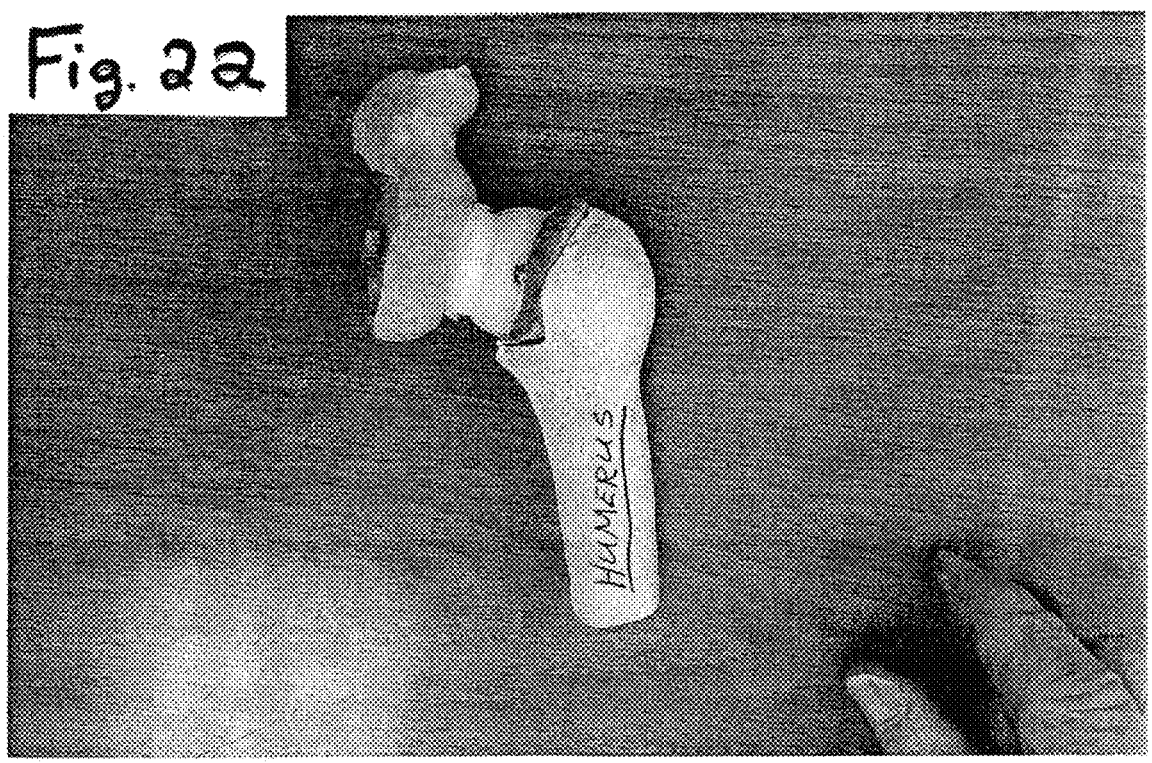

FIG. 22 is a view of the ensemble of FIG. 18, fully assembled from that which is depicted in FIG. 21, and implanted in a human humerus.

Figure 23:
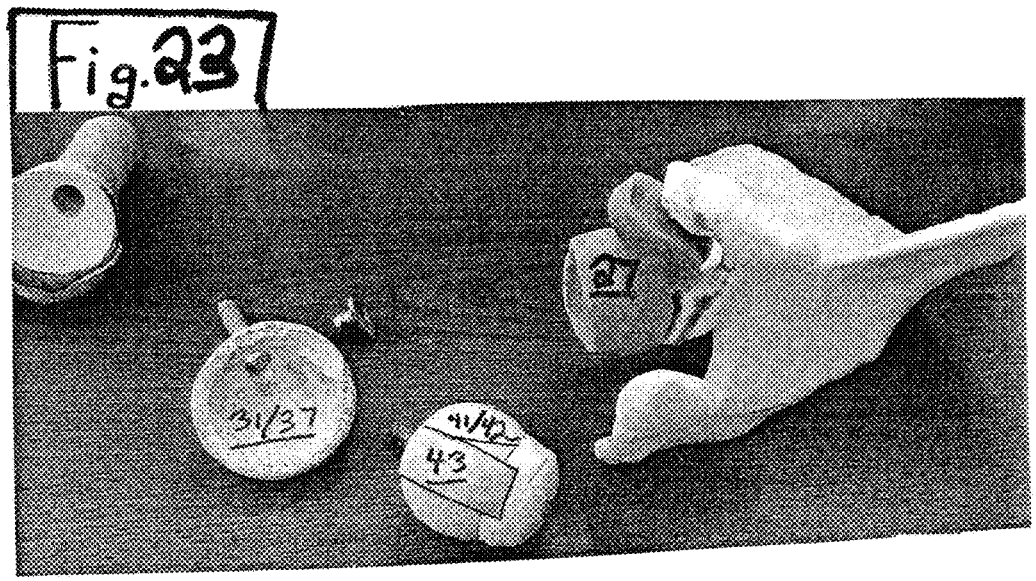

FIG. 23 is an exploded plan view of another embodiment of a universal joint implant ensemble hereof.

Figure 24:
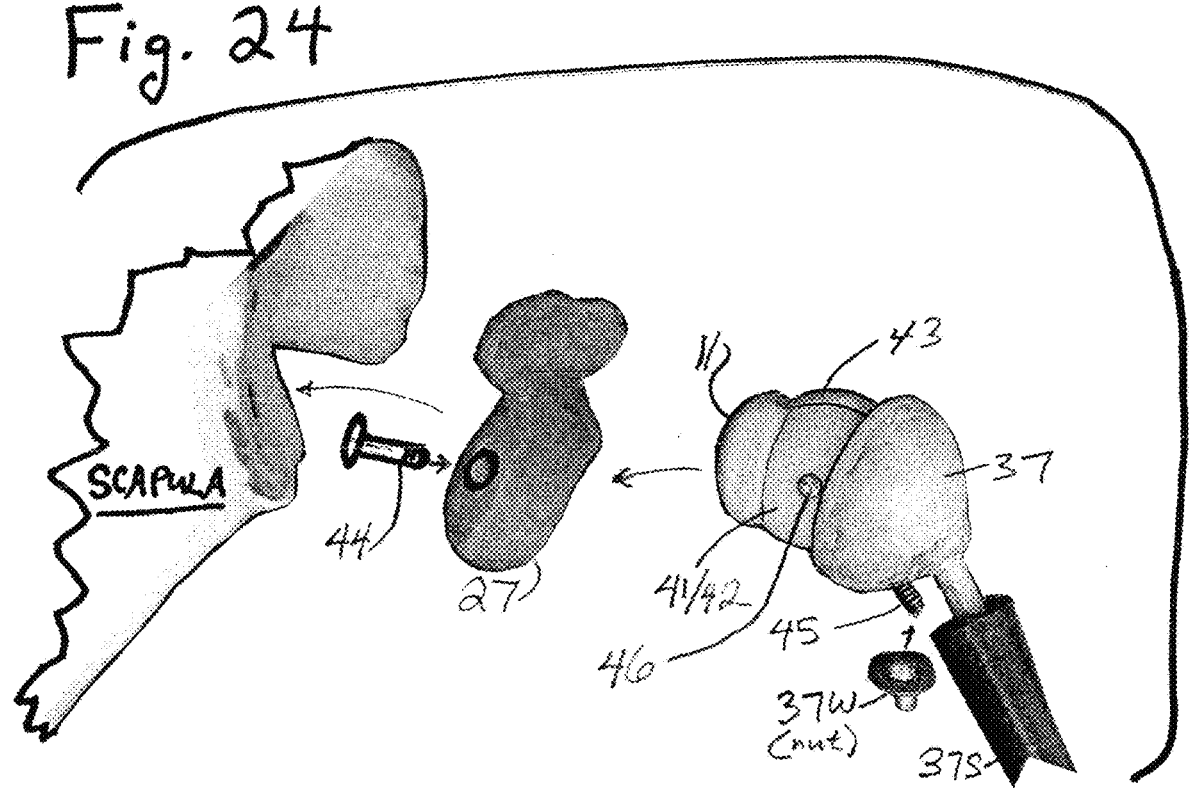

FIG. 24 is exploded view of the ensemble of FIG. 23, in a more ordered state of assembly than that which is depicted in FIG. 23.

Figure 25:
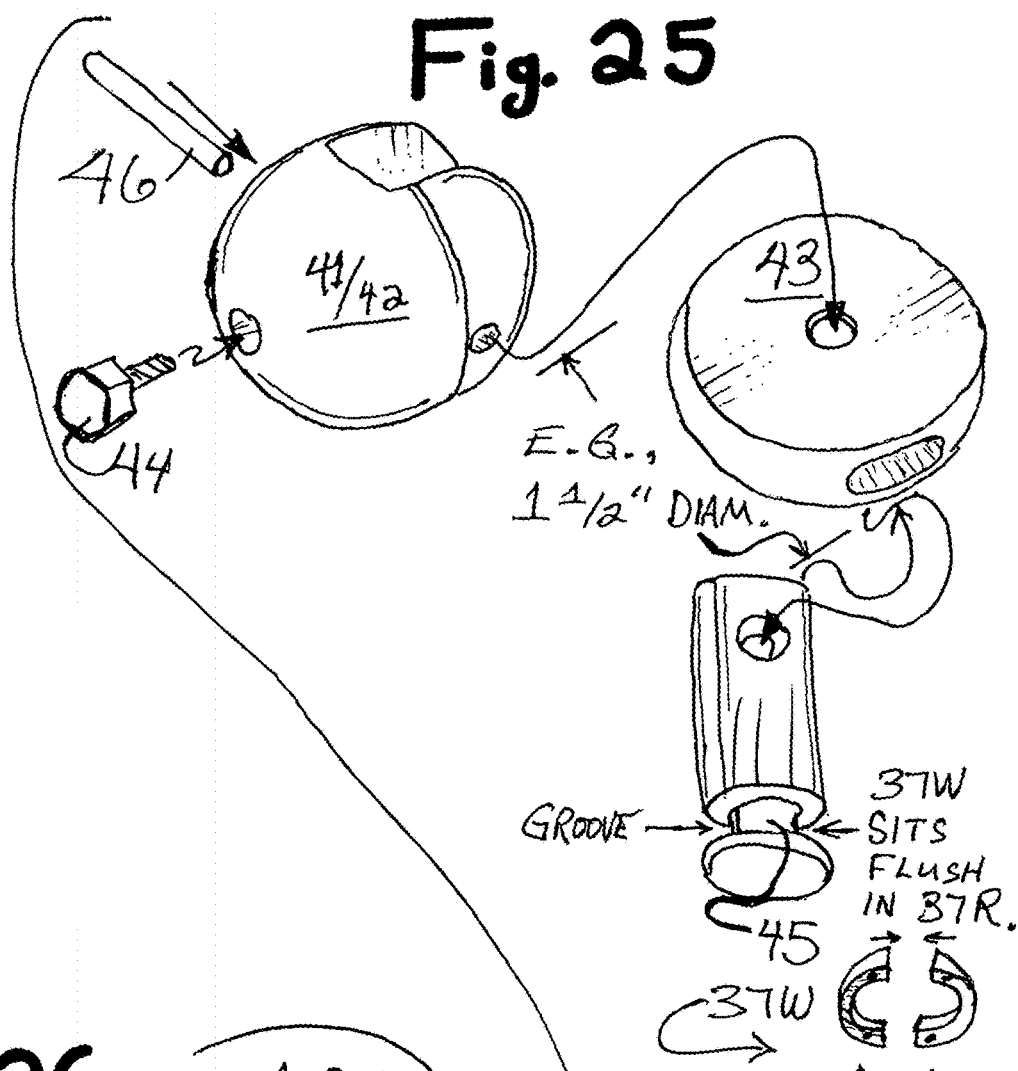

FIG. 25 is an exploded view of a universal joint connection as may be employed in the universal joint implant ensemble of FIG. 18.

Figure 26:
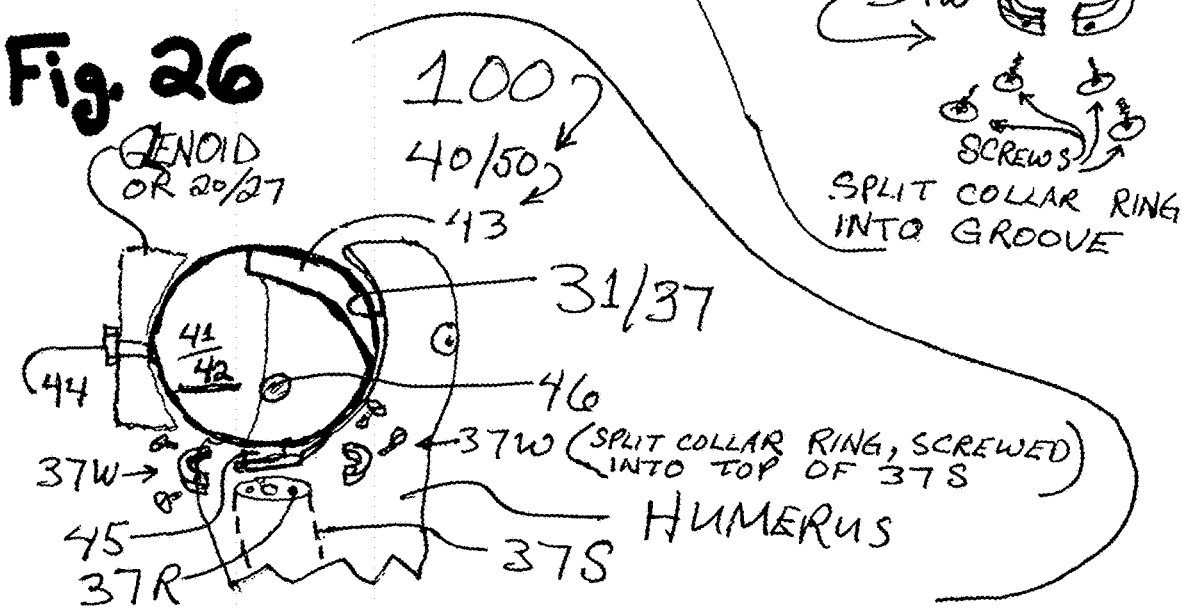

FIG. 26 is a side perspective view of the connection of FIG. 25, in an advanced stage of assembly for illustrative purposes.

Figure 27:
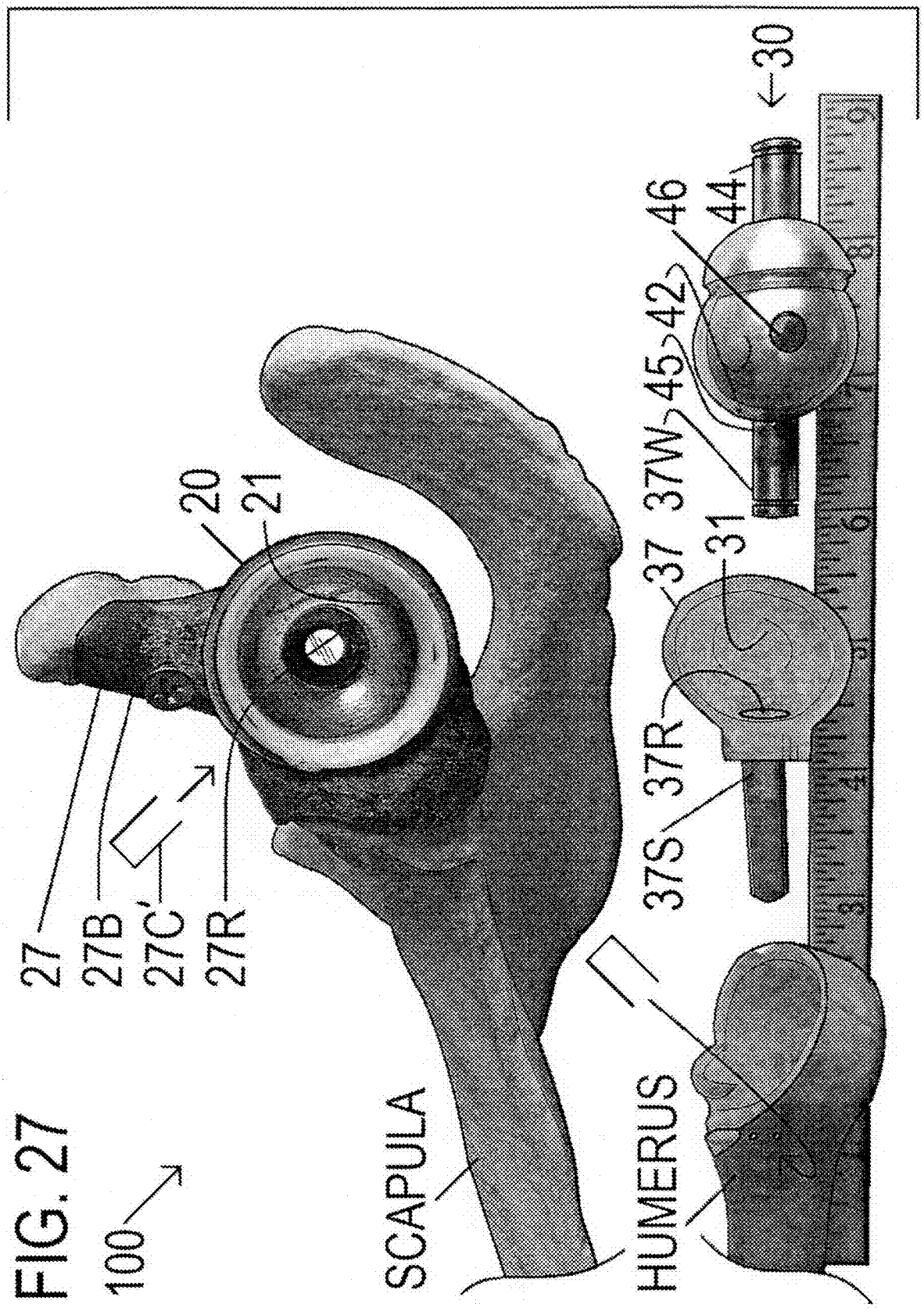

FIG. 27 is an exploded view of another embodiment of a universal joint implant ensemble hereof and resected scapular and humeral bones for implantation thereto. The scale depicted in this figure is set forth in inches.

Figure 28:
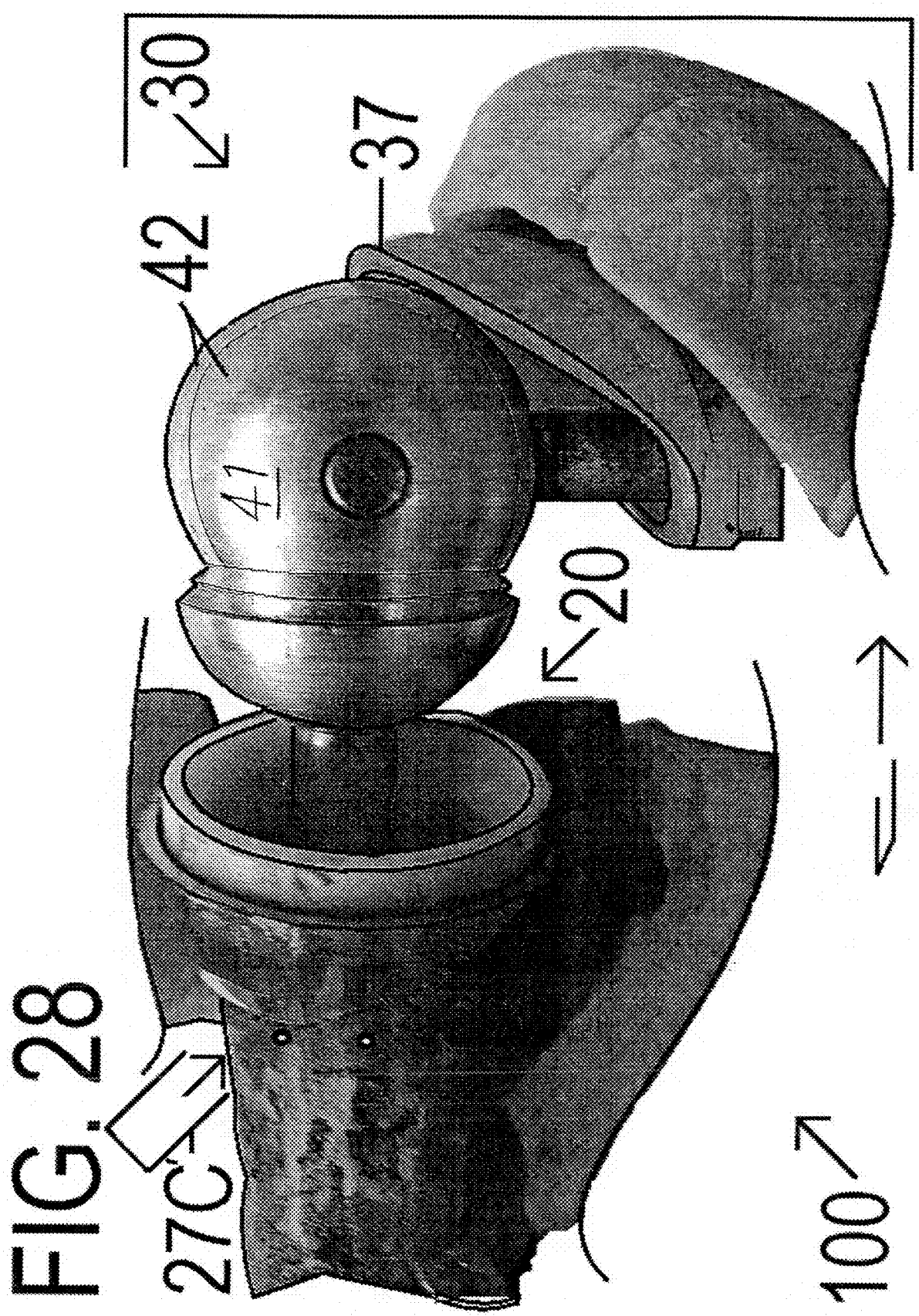

FIG. 28 is an exploded view of the ensemble of FIG. 27, being implanted.

Figure 29:
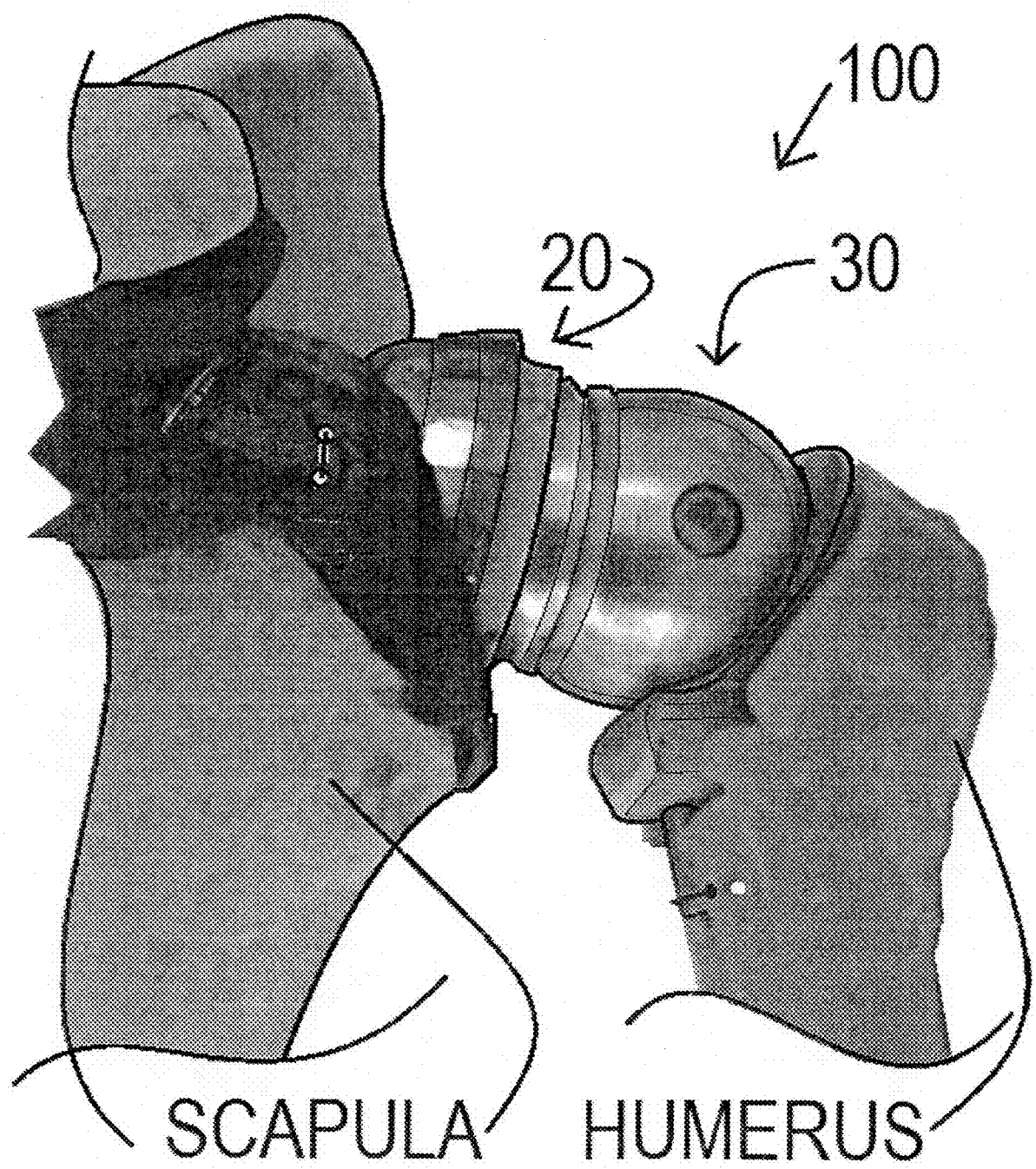

FIG. 29 is a view of the ensemble of FIG. 27, implanted.

The present implant or component can be further understood by the detail below. As with the foregoing, the following may be read in view of the drawings and is to be taken in an illustrative and not necessarily limiting sense.

The present shoulder joint implant or implant component is for implantation as an ensemble for total glenohumeral joint arthroplasty, or at least as a humeral component therefor with attachment to a natural glenoid. An implant component may include provision(s) for bio-ingrowth, may be made to be surgically cementable and through that be surgically cemented and/or be made to be attached to tissue, especially bone, with mechanical fastener attachment such as by bone screw(s), pin(s), staple(s), plate(s), strap(s) and/or suture(s). The glenohumeral joint can be that of a human being.

The implant and its components can be made of any suitable material(s) and method(s) as known to skilled artisans. Biocompatible material(s) is(are) generally employed, which, for instance, may include a suitable metal such as Titanium or alloy thereof, for example, a Titanium-6Aluminum-4Vanadium extra low interstitial (Ti-6Al-4V ELI) alloy for surgical implant applications as specified by ASTM F 136-08 or the like, Cobalt or alloy thereof, for example, a Cobalt-28Chromium-6Molybdenum (Co—Cr) alloy as specified by ASTM F 75-07, ASTM F 799-99 or the like, a non-magnetic cobalt-chromium-molybdenum alloy as a wrought powder metallurgy product, say, BioDur® CCM Plus alloy (Carpenter Technology Corporation), U.S. Pat. No. 5,462,575 to Del Corso and/or a stainless steel as specified by ASTM F 138-08, ASTM F 621-08 or the like; a suitable ceramic such as an alumina or zirconia ceramic, say, a magnesium oxide stabilized transformation toughened zirconia (MgO-TTZ) as set forth in Serafin, Jr. et al., patent No. U.S. Pat. No. 9,259,508 B2, and as may conform to ASTM F 2393-04; and/or a suitable composite or plastic. Bio-ingrowth material(s) may be employed.

The implant and its components can be any suitable size. Custom sizes, which conform to specifics of a certain patient, and standard sizes, which conform to a general class and size of patient, may be provided. Smaller sizes of the substantially spheroidal body, in general, permit the saving of more bone, particularly of a humeral head. Mix and match modularity may be provided.

With reference to the drawings, the following is noted:

Universal joint implant for a shoulder 100 embraces artificial glenohumeral component 50 that may include glenoid component 20 and humeral component 30. It is useful in or as an ensemble for total joint replacement arthroplasty of the glenohumeral joint or in hemiarthroplasty in the glenohumeral joint.

The artificial glenohumeral component 50 has articulating surfaces 10, including first portion 11 for articulation against artificial glenoid surface 21 of the glenoid component 20 or natural glenoid, and second portion(s) 12 for articulation against artificial humeral surface 31 of the humeral component 30 or resected, natural humerus.

The artificial glenohumeral component 50 has universal joint connection 40, which includes yoke 41; substantially spheroidal body 42, at least in part; body 43 pivotable with respect to the yoke 41; rotatable glenoid fixing member 44; and rotatable humeral fixing member 45. Among other things, the yoke 41 can provide for a center of movement generally within and/or adjacent a volume defined by an upper head of a normal humerus, which otherwise would be resected and absent when the artificial glenohumeral component 50 is implanted. The substantially spheroidal body 42 is substantially spheroidal, at least in part, and is dissected and yet connected to provide the yoke 41. The body 43 is pivotable with respect to the yoke to provide for motion in a first direction, typically in a plane cutting through the yoke 41. The rotatable glenoid fixing member 44 is rotatably fixable about the artificial glenoid surface 21 or natural or resected glenoid, and in one embodiment may be connectable to or one with the body 43 that is pivotable with respect to the yoke 41 (FIGS. 1-15). The rotatable humeral fixing member 45 is rotatably fixable about the artificial humeral surface 31 or resected humerus, and in another embodiment may be connectable to or one with the body 43 that is pivotable with respect to the yoke 41 (FIGS. 17-29). Thus, the yoke 41 may be more closely associated with or more directly connectable to the humerus (FIGS. 1-15) or the glenoid (FIGS. 17-29). Pivoting of the body 43 pivotable with respect to the yoke, and in another illustrative embodiment connection of a separable rotatable humeral fixing member 45, which otherwise could apply analogously to a separable rotatable glenoid fixing member, can be achieved by provision of pivot pin 46 that can pass through the body 43, the yoke 41 and, in certain embodiments, the separable rotatable fixing member, for example, the separable rotatable humeral fixing member 45. The components 41, 42, 43, 44, 45 and/or 46 and so forth can be closely fitting.

Additional component(s) may be provided. For instance, the glenoid component 20 may embrace glenoid augment 27, which can function as a glenoid corticoid stabilization member, and include main body 27B and slide-in closure 27C for enclosing glenoid receptacle 27R to receive the rotatable glenoid fixing member 44 rotatably. A staple 27C' set screw(s) or pin(s) may be employed in lieu of or in addition to the slide-in closure 27C. The glenoid augment 27 can provide the artificial glenoid surface 21, which may have an articulating surface in a form of a glenoid cup. As well, the humeral component 30 may embrace humeral augment 37 that provides the artificial humeral surface 31, which may have an articulating surface in a form of a cup, a flat surface, and/or humeral receptacle 37R, say, having a cylindrical or tapered surface, which may or even be provided with an expanded extremity to hold the rotatable humeral fixing member 45 in place in or with respect to the humerus. The humeral receptacle 37R can be provided to receive the rotatable humeral fixing member rotatably, for example, in the interior of intramedullary humeral stem 37S, which may include the humeral receptacle. Rotatable humeral fixing member withholding system 37W can be provided to assist in holding the artificial glenohumeral component 50 to the humerus. For example, the rotatable humeral fixing member withholding system 37W can include a circumferential groove in a depending shaft of the rotatable humeral fixing member 45 into which set screw(s), pin(s) or staple(s) can be positioned; an annular circumferential groove in the humeral receptacle 37R facing a corresponding circumferential groove in a depending shaft of the rotatable humeral fixing member 45, into which a locking ring spring can be positioned; an annular circumferential groove in the humeral receptacle 37R into which a flaring head or flange on a depending shaft of the rotatable humeral fixing member 45, which may be a movable outwardly biased head or flange, or which may be immobile with respect to the rest of the depending shaft and have a closure akin to the slide-in closure 27C or staple(s) 27C' set screw(s) or pin(s) provided as part of or in conjunction with the intramedullary humeral stem 37S, or which may be provided with a nut to screw onto a terminal end of the depending shaft; and so forth and the like. Corresponding system(s) may be provided for the glenoid. Multi-point fixation, for example, with the glenoid component 20 may be provided with arm(s) 235, which may include acromion fixing arm 235A and/or coracoid process fixing arm 235C, any of which may be provided with hole 235H for fixation with a fastener such a bone screw. Bone screw(s), with or without washer(s) may be employed in other locations as or with the additional component(s). As mentioned, bio-ingrowth material(s) may be employed; the same may be a material such as a porous coating or a coating of hydroxyapatite for ingrowth of bone. The additional component(s), especially when moveable or having moveable part(s) moving against the same, may be closely fitting as well.

Surgical implantation of the present implant can be carried out by a person skilled in the art of orthopedic surgery. Bone resection is typically carried out, particularly to accommodate components of the universal joint implant for a shoulder 100. Surgical cement may be employed.

Numerical values herein may be considered to be approximate or exact.

The terms, "fixable" and "fixing," may be replaced, respectively, with, "securable" and "securing." Thus, for example, the terms, "rotatably fixable" and "fixing member," may be considered to be rendered respectively as "rotatably securing" and "securing member."

INCORPORATIONS OF U.S. PATENTS

Each of U.S. Pat. No. 5,462,575 to Del Corso, U.S. Pat. No. 9,529,508 B2 to Serafin, Jr. et al., and U.S. Pat. No. 9,561,111 B1 to Goodman is incorporated herein by reference in its entirety, to include drawings.

CONCLUSION TO THE INVENTION

The present invention is thus provided. Various feature(s), part(s), step(s), subcombination(s) and/or combination(s) may be employed with or without reference to other feature(s), part(s), step(s), subcombination(s) and/or combination(s) in the practice of the invention, and numerous adaptations and modifications can be effected within its spirit, the literal claim scope of which is particularly pointed out as follows:

I claim:

1. A universal joint implant for a shoulder of a patient, which comprises an artificial glenohumeral component, which is configured to be useful in or as an ensemble for total joint replacement arthroplasty of the glenohumeral joint or in hemiarthroplasty in the glenohumeral joint, wherein:
   the artificial glenohumeral component has a member having articulating surfaces, with the articulating surfaces of the member including a first portion configured for articulation against a concave artificial glenoid articulating surface or a natural glenoid articulating surface of the patient, and second portion(s) configured for articulation against corresponding concave artificial humeral articulating surface(s) or a natural humerus of the patient, which is resected to provide corresponding concave humeral articulating surface(s) therein; and
   the artificial glenohumeral component has a universal joint connection, which includes the following:
      a yoke, which provides for a center of movement generally within or adjacent a volume defined by an upper head of a normal humerus, which otherwise would be resected and absent when the the artificial glenohumeral component is implanted;
      as the member having articulating surfaces, a substantially spheroidal body, at least in part, having a channel therein configured to receive a body pivotable with respect to the yoke for providing motion in a first direction, with the at least in part substantially spheroidal body further configured to do the following:
         receive a pivot member passing through the channel and the body pivotable with respect to the yoke in order to provide the yoke when the body pivotable with respect to the yoke is received in the channel, and the pivot member passes through the channel and the body pivotable with respect to the yoke; and
         have the first portion and the second portion(s) of the articulating surfaces of the member having articulating surfaces on substantially spheroidal surfaces of the at least in part substantially spheroidal body;
      the body pivotable with respect to the yoke for providing motion in a first direction;
      the pivot member;
      a rotatable glenoid securing member, rotatably securable about the artificial glenoid surface or natural or resected glenoid and connectable to the member having articulating surfaces; and
      a rotatable humeral securing member, rotatably securable about the artificial humeral surface or resected humerus and connectable to the member having articulating surfaces; and
   the universal joint connection allows limited freedom of movement in any direction while transmitting rotary motion.

2. The universal joint implant of claim 1, which further includes at least one additional component selected from the group consisting of the following features (A-D):
   (A) a glenoid augment that provides the artificial glenoid surface, which has an articulating surface in a form of a glenoid cup;
   (B) a glenoid receptacle provided to receive the rotatable glenoid securing member rotatably;
   (C) a humeral augment that provides the artificial humeral surface, which has an articulating surface in a form of a cup for resected humerus; and
   (D) a humeral receptacle to receive the rotatable humeral securing member rotatably.

3. The universal joint implant of claim 1, which is configured to be useful in or as the ensemble for total joint replacement arthroplasty of the glenohumeral joint.

4. The universal joint implant of claim 2, which is configured to be useful in or as the ensemble for total joint replacement arthroplasty of the glenohumeral joint.

5. The universal joint implant of claim 2, wherein all of features A, B, C and D are present.

6. The universal joint implant of claim 4, wherein all of features A, B, C and D are present.

7. The universal joint implant of claim 1, wherein the rotatable glenoid securing member is rotatably securable about the artificial glenoid surface or natural or resected glenoid, and is connectable to or one with the body that is pivotable with respect to the yoke.

8. The universal joint implant of claim 2, wherein the rotatable glenoid securing member is rotatably securable about the artificial glenoid surface or natural or resected glenoid, and is connectable to or one with the body that is pivotable with respect to the yoke.

9. The universal joint implant of claim 3, wherein the rotatable glenoid securing member is rotatably securable about the artificial glenoid surface or natural or resected glenoid, and is connectable to or one with the body that is pivotable with respect to the yoke.

10. The universal joint implant of claim 4, wherein the rotatable glenoid securing member is rotatably securable about the artificial glenoid surface or natural or resected glenoid, and is connectable to or one with the body that is pivotable with respect to the yoke.

11. The universal joint implant of claim 5, wherein the rotatable glenoid securing member is rotatably securable about the artificial glenoid surface or natural or resected glenoid, and is connectable to or one with the body that is pivotable with respect to the yoke.

12. The universal joint implant of claim 6, wherein the rotatable glenoid securing member is rotatably securable about the artificial glenoid surface or natural or resected glenoid, and is connectable to or one with the body that is pivotable with respect to the yoke.

13. The universal joint implant of claim 1, wherein the rotatable humeral securing member is rotatably securable about the artificial humeral surface or resected humerus, and is connectable to or one with the body that is pivotable with respect to the yoke.

14. The universal joint implant of claim 2, wherein the rotatable humeral securing member is rotatably securable about the artificial humeral surface or resected humerus, and is connectable to or one with the body that is pivotable with respect to the yoke.

15. The universal joint implant of claim 3, wherein the rotatable humeral securing member is rotatably securable about the artificial humeral surface or resected humerus, and is connectable to or one with the body that is pivotable with respect to the yoke.

16. The universal joint implant of claim 4, wherein the rotatable humeral securing member is rotatably securable about the artificial humeral surface or resected humerus, and is connectable to or one with the body that is pivotable with respect to the yoke.

17. The universal joint implant of claim 5, wherein the rotatable humeral securing member is rotatably securable about the artificial humeral surface or resected humerus, and is connectable to or one with the body that is pivotable with respect to the yoke.

18. The universal joint implant of claim 6, wherein the rotatable humeral securing member is rotatably securable about the artificial humeral surface or resected humerus, and is connectable to or one with the body that is pivotable with respect to the yoke.

19. A universal joint implant for a shoulder of a patient, which comprises an artificial glenohumeral component that includes a glenoid component and a humeral component, which is useful in or as an ensemble for total joint replacement arthroplasty of the glenohumeral joint or in hemiarthroplasty in the glenohumeral joint of the human patient, wherein:

the artificial glenohumeral component has a first body having articulating surfaces, with the articulating surfaces of the first body including a first portion configured for articulation against a concave artificial glenoid articulating surface of the glenoid component or a natural glenoid articulating surface of the patient, and second portion(s) configured for articulation against corresponding concave artificial humeral articulating surface(s) of the humeral component or a natural humerus of the patient, which is resected to provide corresponding concave humeral articulating surface(s) therein;

the artificial glenohumeral component has a universal joint connection, which allows limited freedom of movement in any direction while transmitting rotary motion, and which includes a yoke that provides for a center of movement generally within and/or adjacent a volume defined by an upper head of a normal humerus, which otherwise would be resected and absent when the artificial glenohumeral component is implanted; the first body, a second body, and a pivot pin, wherein the first body that is substantially spheroidal, at least in part, and has a channel therein configured to receive the second body, the second body being pivotable with respect to the yoke to provide for motion in a first direction in a plane cutting through the yoke and being configured to receive the pivot pin, which passes through the channel and the second body to provide the yoke, and wherein the first body is further configured to have the first portion and the second portion(s) of the articulating surfaces on substantially spheroidal surfaces of the first body; a rotatable glenoid securing member, which is rotatably securable about the artificial glenoid surface or natural or resected glenoid and connectable to the first body; and a rotatable humeral securing member, which is rotatably securable about the artificial humeral surface or resected humerus and connectable to the first body; and the patient is human.

20. The universal joint implant of claim 19, wherein at least one of the following features (A-F) is present:

(A) the glenoid component includes a glenoid augment, which can function as a glenoid corticoid stabilization member, and include a main body and a slide-in closure for enclosing a glenoid receptacle to receive the rotatable glenoid securing member rotatably;

(B) the glenoid component includes staple(s), set screw(s) and/or pin(s) to hold the rotatable glenoid securing member rotatably with respect to a groove in the glenoid securing member;

(C) the glenoid augment provides the artificial glenoid surface, which has an articulating surface in a form of a glenoid cup;

(D) the humeral component includes a humeral augment, which provides the artificial humeral surface, and which has an articulating surface in a form of at least one of a cup and a flat surface;

(E) the humeral component includes as the humeral augment a receptacle having a cylindrical or tapered surface to receive the rotatable humeral securing member rotatably in the interior of intramedullary humeral stem; and (F) a rotatable humeral securing member withholding system, which assists in holding the artificial glenohumeral component to the humerus, which includes a circumferential groove in a depending shaft of the rotatable humeral securing member into which set screw(s), pin(s) and/or staple(s), a locking ring spring, or a flaring head or flange is/are provided.

* * * * *

UNITED STATES PATENT AND TRADEMARK OFFICE
CERTIFICATE OF CORRECTION

| | | |
|---|---|---|
| PATENT NO. | : 10,524,921 B2 | Page 1 of 1 |
| APPLICATION NO. | : 15/932543 | |
| DATED | : January 7, 2020 | |
| INVENTOR(S) | : Goodman | |

It is certified that error appears in the above-identified patent and that said Letters Patent is hereby corrected as shown below:

In the Claims

In Claim 19, Line 6, i.e., Column 9, Line 16, immediately preceding the word, "patient," delete the word, "human."

Signed and Sealed this
Twenty-eighth Day of April, 2020

Andrei Iancu
*Director of the United States Patent and Trademark Office*